United States Patent
Kudis et al.

(10) Patent No.: US 7,314,948 B2
(45) Date of Patent: Jan. 1, 2008

(54) METHOD FOR PRODUCING ALKYL NITRITES AND ALKYL DINITRITES

(75) Inventors: Steffen Kudis, Mannheim (DE); Rene Lochtman, Mannheim (DE); Manfred Ehresmann, Ludwigshafen (DE); Michael Keil, Freinsheim (DE); Joachim Gebhardt, Wachenheim (DE); Michael Rack, Heidelberg (DE); Ralf Schimetzek, Speyer (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 522 days.

(21) Appl. No.: 10/485,209

(22) PCT Filed: Aug. 2, 2002

(86) PCT No.: PCT/EP02/08639

§ 371 (c)(1),
(2), (4) Date: Jan. 29, 2004

(87) PCT Pub. No.: WO03/014059

PCT Pub. Date: Feb. 20, 2003

(65) Prior Publication Data

US 2004/0199003 A1    Oct. 7, 2004

(30) Foreign Application Priority Data

Aug. 3, 2001  (DE)  ................. 101 38 152

(51) Int. Cl.
*C07C 23/02* (2006.01)

(52) U.S. Cl. .................................................. 558/488
(58) Field of Classification Search ................. 558/488
See application file for complete search history.

(56) References Cited

U.S. PATENT DOCUMENTS

| 2,714,606 | A | 8/1955 | Soloveichik |
| 3,792,077 | A | 2/1974 | Bermes |
| 4,980,496 | A | 12/1990 | Fruchey |

FOREIGN PATENT DOCUMENTS

| DE | 1043310 | 3/1953 |
| WO | WO01/74754 | 10/2001 |

OTHER PUBLICATIONS

Noyes, W.A. "n-Butyl Nitrite" Organic Syntheses Collective, vol. 2, 1953, pp. 108-109.*
McMurry, John "Organic Chemistry—Fourth Edition" Brooks/Cole Publishing Company, 1996, p. 411.*
Organic Syntheses, Noyes, Collective vol. 2 108-109, PY=1953.
Callen et al., Organic Syntheses Coll. vol. 3, pp. 26-28 (1955): "*9-Acetylphenanthrene*".

* cited by examiner

*Primary Examiner*—Kamal A. Saeed
*Assistant Examiner*—Joseph R. Kosack
(74) *Attorney, Agent, or Firm*—Novak Druce & Quigg, LLP

(57) ABSTRACT

In a continuous process for the preparation of alkyl nitrites and dinitrites, an alkanol or dialkanol is first mixed with an aqueous mineral acid, the reaction mixture obtained is then reacted with an inorganic nitrite and the product obtained can then be isolated immediately.

12 Claims, No Drawings

METHOD FOR PRODUCING ALKYL NITRITES AND ALKYL DINITRITES

The present invention relates to a continuous process for the preparation of alkyl nitrites and dinitrites by reaction of alkanols or dialkanols with nitrite ions in the presence of an aqueous mineral acid.

Alkyl nitrites and dinitrites are important nitrosation reagents in preparative chemistry. They are used, for example, to prepare diazonium compounds from primary amines. Particularly aromatic diazonium compounds are important intermediates, since the diazonium group can be converted into a multitude of substituents such as pseudohalogen, halogen (Sandmeyer reaction, Schiemann reaction), hydroxyl, mercapto or hydrogen. Diazonium compounds are further used as starting materials in phenanthrene ring closures (Pschorr reaction), for the preparation of aryl hydrazones (Japp-Klingemann reaction), of aryl hydrazines or of azo compounds.

DE 21 444 20 describes a batchwise process for the preparation of glycols and glycol derivatives, in which glycols or glycol derivatives are stirred with sodium nitrite and ice-water and hydrochloric acid is then added, with the temperature being held below 10° C. by means of external cooling.

Organic Syntheses Coll. vol. 2, 108 (1943) describes the preparation of n-butyl nitrite, in which a mixture of water, iso-propanol and sulfuric acid is added to aqueous sodium nitrite. A disadvantage of this process is the formation of a three-phase mixture with solid sodium sulfate in the third phase.

U.S. Pat. No. 4,980,496 describes a batchwise process for the preparation of alkyl nitrites, where an aqueous solution of a $C_1$-$C_5$-alkanol is mixed with an alkali metal nitrite, the mixture is cooled to about −10 to 10° C. and then a hydrohalic acid is added while the temperature is kept constant. The hydrohalic acid is generally used in excess, in particular of about 4 mol % based on the alcohol, in order to achieve a complete conversion.

The process of U.S. Pat. No. 4,980,496 is problematic in various respects. Firstly, the reaction is exothermic, so that it is difficult to hold the reaction temperature in the range from −10 to 10° C. Secondly, alkyl nitrites in a strong acidic medium tend to decompose and form by-products, so that the acid excess necessary for the reaction must be neutralized, or the product must immediately be separated from the aqueous phase and stored under suitable drying conditions.

Investigations carried out by the assignee have in turn shown that the reduction of the acid quantity in the batchwise process leads to increased formation of by-products such as acetals and ketals and to a reduction in the yield.

It is an object of the present invention to provide a process for the preparation of alkyl nitrites and dinitrites whereby these compounds can be prepared in a simple way and with increased purity and also good storage stability. Ideally, the process shall have no special equipments and preparative requirements in order that costs may be minimised.

We have found that this object is achieved when an alkanol or dialkanol is mixed with the aqueous solution of a mineral acid using on average not more than 1.01 mol of acid equivalents per mole of hydroxyl group of the alkanol or dialkanol is used and an aqueous solution of an inorganic nitrite is continuously added to this mixture.

Therefore, the present invention provides a process for continuous preparation of alkyl nitrites and alkyl dinitrites by reaction of an alkanol or a dialkanol with an inorganic nitrite in the presence of at least one mineral acid that does not oxidize nitrite, wherein (i) the alkanol or dialkanol is mixed with an aqueous solution of the mineral acid using on average not more than 1.01 mol of acid equivalents per mole of hydroxyl group in the alkanol or dialkanol is used, (ii) an aqueous solution of the inorganic nitrite is added continuously to the aqueous mixture obtained in (i) in a reaction zone, and (iii) the organic phase is optionally isolated.

Examples of aqueous mineral acids that do not oxidize nitrite include dilute sulfuric acid, phosphoric acid and hydrohalic acids, e.g. hydrogen chloride, hydrogen bromide or hydrogen iodide. In a preferred embodiment, hydrogen chloride in water (hydrochloric acid) is used. The concentration of hydrogen chloride in water can be varied within a wide range. In general it is in the range from 10 to 40% by weight, preferably from 15 to 35% by weight. Technical grade hydrochloric acid is customarily used.

Suitable alkanols and dialkanols are those that have at least some solubility in water. These include $C_2$ to $C_6$ alkanols, such as ethanol, n-propanol, isopropanol, n-butanol, sec-butanol, isobutanol, tert-butanol, n-amyl alcohol, isoamyl alcohol (3-methyl-1-butanol), 2-methyl-1-butanol, n-hexanol, 2-hexanol and 2-methyl-1-pentanol.

Suitable dialkanols are selected from the group consisting of $C_2$ to $C_6$ dialkanols such as 2,2-dimethyl-1,3-propanediol, 1,4-butanediol, 1,5-pentanediol, especially 2,2-dimethyl -1,3-propanediol.

The present invention is particularly suitable for the reaction of n-butanol, tert-butanol and isoamyl alcohol.

The alkanol or dialkanol is generally used in an undiluted form. A solvent may also be used, and water is preferable. In principle, it is also possible to use any solvents that are miscible with water can be used, that are inert toward acidic nitrite and that do not restrict the use of the reaction products, e.g. cyclic ethers such as dioxane or tetrahydrofuran, or ketones such as acetone and methyl ethyl ketone.

Customarily, the concentrations of aqueous mineral acid and alkanol or dialkanol are selected such that on average not more than 1.01 mol, preferably from 1.00 to 1.005 mol of mineral acid equivalents per mole of hydroxyl group in the alkanol or dialkanol are used. In a very particularly preferred embodiment of the invention, an equimolar quantity of the mineral acid per mole of hydroxyl group in the alkanol or dialkanol is used.

The mixing of the alkanol and aqueous mineral acid can be carried out by the usual means. The mixing temperature is relatively unimportant for the success of the invention. In general, the temperature of the mixture is set at that required for the subsequent reaction with the nitrite, i.e. at a temperature preferably in the range from 5 to 40° C., in particular in the range from 10 to 30° C., especially in the range from 15 to 25° C. If necessary, the mineral acid and the alkanol are precooled to the desired temperature. The mixing of the alkanol or dialkanol and the mineral acid can take place in a container, in a mixing chamber or via static mixers in a pipe. When a mixing container is used for the preparation of the mixture, it can be carried out either continuously or batchwise. The mixing can be carried out by stirring or by mixing of streams. In one embodiment of the invention, the alkanol or dialkanol are continuously fed into a container with mixing, preferably into a stirred-tank vessel, and continuously removed therefrom.

In the second step (ii) of the present process, an aqueous solution of the inorganic nitrite is continuously added to the aqueous mixture obtained in (i) in a reaction zone.

Suitable sources of nitrite ions are inorganic nitrites, e.g. alkali metal and alkaline earth metal nitrites such as sodium, potassium, barium and calcium nitrite, and also ammonium nitrite. Of these, potassium nitrite and especially sodium nitrite are particularly preferred.

The quantity of inorganic nitrite added in the second step (ii) dissolved in water substantially corresponds to the required stoichiometry, although the nitrite can also be used in an excess that in general does not exceed 20 mol %. The stoichiometry is based on the amount of hydroxyl group in the alkanol or dialkanol used. The molar ratio of hydroxyl group in the alkanol or dialkanol to inorganic nitrite generally is in the range from 1:1.0 to 1:1.2, preferably 1:1.01 to 1.2 and in particular 1:1.05 to 1:1.12.

In general the total quantity of water in the second step (ii) is 1 to 5 times, preferably 1.5 to 4 times and in particular 2.5 to 3.5 times the volume of the organic phase.

To carry out step (ii), the mixture obtained in (i) and the aqueous nitrite solution are introduced into a reaction zone which has the desired temperature. The reaction zone generally comprises one or more, successive reaction tanks (tank battery) or reaction tubes, and tanks and tank batteries are preferred. The reaction zones generally have standard means for mixing liquids, e.g. static mixers such as internals and/or stirrers and/or means for pumping liquids, preferably in combination with the static mixers. Mixing of the alcohol/acid mixture and the nitrite solution can also be carried out by introducing the liquid reactants to the second step (ii) by means that are suitable for the continuous mixing of liquids. In the case of relatively smaller apparatus dimensions, mixing of the reactants can also be achieved by introducing the liquid reactants into the reactor with vortexing of streams of liquid, for example through two immediately adjacent inlets for the streams of liquid. This method has proved itself particularly in laboratory and "Miniplant" plants having reactor volumes (volumes of the respective reaction zone) of ≦1000 ml, preferably ≦200 ml.

Further, the reaction zone generally has standard means for removal of the heat of reaction, e.g. cooling coils, wall coolers and the like.

The residence time of the reactants in the reaction zone is in general in the range from 20 minutes to 5 hours, preferably 25 min to 3 hours, in particular 40 min to 2 hours and very particularly preferably 40 min to 60 min. The residence time is by its nature dependent upon the addition rate of the reactants. Normally, a longer residence time is chosen at low reaction temperatures and a shorter residence time is chosen at higher reaction temperatures.

The reaction temperature for the conversion of the alkanol or dialkanol into the corresponding alkyl nitrite or dinitrite in the second step (ii) is preferably in the range from 5 to 40° C., in particular 10 to 30° C. and especially 15 to 25° C.

The reaction mixture occurring at the downstream end of the reaction zone generally has a pH of above 3.

In a preferred embodiment of the invention, the reaction zone in step (ii) comprises at least two reaction tanks (battery). The mixture obtained in step (i) and the aqueous inorganic nitrite solution are fed separately and continuously into a first reactor. The contents of the first reactor are mixed by standard means, e.g. by stirring, intensive circulation or by injection of the reactants. The mixture is transferred by means of a discharging device, e.g. an overflow, into at least one further reactor to complete the reaction, after a residence time determined by the relationship between the reactor volume and the introduction and withdrawal rates. This method is particularly advantageous in the case of reactor volumes of at least 200 ml.

The product of value can be separated off directly after step (ii). In general, the reaction mixture is biphasic and readily separates. The removal of the product of value can be carried out by the standard techniques, for example by introduction of the reaction effluent from step (ii) into a phase-separating vessel. The removal is normally carried out at room temperature. The steps (i) to (iii) are normally carried out at atmospheric pressure. The alkyl nitrite or dinitrite obtained generally has a GC (FID) purity of greater than 95%, very frequently greater than 97% and more often than not greater than 98%. The yield of the product of value is only slightly below the GC purities obtained.

The process of the invention has the advantage over the batchwise processes of the prior art that the alkyl nitrite or dinitrite can be prepared with the use of a smaller excess of acid or without an excess of acid without loss of product quality and yield, so that the disadvantages of the prior art outlined at the beginning are overcome. Furthermore, the continuous process allows a more efficient and rapid production of larger product quantities. Removal of the products of value is not necessary, in contrast to the prior art batch processes, or only in those cases where the use of water-free alkyl nitrite on dinitrite is required. The storage stability of the alkyl nitrite or dinitrite obtained is also better.

Furthermore, the process of the invention is more economical, since in contrast to the batchwise processes, little cooling if any is necessary during the reaction. Also, the aqueous phase does not need to be separated from the product phase immediately after the reaction. Rather, it is even possible to store the product phase over the water phase at room temperature for a limited period of several days, with only negligible decomposition occurring.

The process of the invention is illustrated by the following examples.

EXAMPLE 1

A 5 l glass feed vessel was charged with n-butanol and a second 5 l glass feed vessel was charged with 20% by weight of hydrochloric acid, and each were pumped by a membrane pump in a molar ratio of 1:1 into a 0.75 l glass stirred reactor.

219.5 g/h of this mixture of n-butanol and hydrochloric acid and an aqueous 40% by weight sodium nitrite solution were pumped synchronously into a first 0.75 l glass stirred reactor. The molar ratio of n-butanol to hydrochloric acid to sodium nitrite was 1:1:1.1. The mixture was transferred through an overflow into a second 0.75 l glass stirred reactor after a residence time determined by the addition time. The total residence time of the reactants was about 45 to 50 min. The reaction mixture was finally transferred through an overflow into a separating funnel. The n-butyl nitrite was separated off according to GC (FID) contained 0.77% of butanol. The purity of the product of value was, according to GC (FID), 98.87%. The quantity of dibutoxybutane was below 0.1%. The product was stable for several days over the aqueous phase.

EXAMPLE 2

Example 1 was repeated, except that the butyl nitrite was not separated from the aqueous phase until after 6 days. The storage over the aqueous phase was carried out at 5° C. The degree of decomposition of the n-butyl nitrite was below 0.1%. Similar results were obtained after storage at 20° C.

EXAMPLE 3 COMPARATIVE EXAMPLE

Example 1 was repeated, except that the addition rate of the mixture of HCl/BuOH was 324 g/h, and the molar ratio of butanol:HCl was 1:1.1. The purity of the product of value was 98.62% by GC (FID). The product of value contained 1.01% of butanol.

EXAMPLE 4 COMPARATIVE EXAMPLE

Example 3 was repeated, except that the addition rate of the mixture of HCl/BuOH was 233 g/h. Further, a 32% by weight solution of hydrochloric acid was used. The purity of the product of value was 98.72% by GC (FID). The product of value contained 0.93% of butanol.

EXAMPLE 5 COMPARATIVE EXAMPLE

Example 4 was repeated, except that the addition rate of the mixture of HCl/BuOH was 232 g/h. Also, step (ii) was carried out at an internal reaction temperature of 10° C. The purity of the product of value was 98.72% by GC (FID). The product of value contained 0.97% of butanol.

EXAMPLE 6 COMPARATIVE EXAMPLE

Example 5 was repeated, except that step (ii) was carried out at an internal reaction temperature of 0° C. The purity of the product of value was 99.02% by GC (FID). The product of value contained 0.93% of butanol.

EXAMPLE 7 COMPARATIVE EXAMPLE

Example 1 was repeated, except that the addition rate of the mixture of HCl/BuOH was 203.5 g/h, and the molar ratio of butanol:HCl was 1:1.05. Also, step (ii) was carried out at an internal reaction temperature of −10° C. The purity of the product of value was 98.86% by GC (FID). The product of value contained 0.88% of butanol. If the product was not separated immediately from the aqueous phase, decomposition to n-butanol and the formation of dibutoxybutane (up to 3%) took place at 5° C. within about 2 days.

EXAMPLE 8 COMPARATIVE, BATCHWISE PROCESS

A tank was charged with 81.5 kg (1100 mol) of n-butanol and cooled to −5° C. 125.3 kg (1115 mol) of 32.4% hydrochloric acid were added over 2.25 hours such that the temperature in the tank remained constantly below −5° C. The contents of the tank were then cooled at −15° C. and 208.2 kg (1210 mol) of a 40% sodium nitrite solution that had been cooled to 8 to 12° C. were added with stirring over the course of about 6 hours so that the temperature remained below −5° C. Once addition was complete, stirring was continued for a further 15 min at from −10 to −5° C., the stirrer was switched off in order to separate the phases and the organic phase was separated off. The yield of n-butyl nitrite was 98.5% in a purity by GC (FID) of 98.25%. The product also contained 0.73% butanol by GC (FID). If the product was not immediately separated from the aqueous phase, decomposition to n-butanol and the formation of dibutoxybutane (up to 3%) occurred at 5° C. within about 2 days.

We claim:

1. A process for continuous preparation of alkyl nitrites and alkyl dinitrites by reaction of an alkanol or a dialkanol with an inorganic nitrite in the presence of at least one mineral acid that does not oxidize nitrite, wherein
   (i) the alkanol or dialkanol is mixed with an aqueous solution of the mineral acid using on average not more than 1.01 mol of acid equivalents per mole of hydroxyl group in the alkanol or dialkanol,
   (ii) an aqueous solution of the inorganic nitrite is added continuously to the aqueous mixture obtained in (i) in a reaction zone, and
   (iii) the organic phase is optionally isolated.

2. The process as claimed in claim 1, wherein the aqueous mineral acid in step (i) is hydrochloric acid.

3. The process as claimed in claim 2, wherein the concentration of hydrogen chloride in water is in the range from 10 to 40% by weight.

4. The process as claimed in claim 1, wherein the inorganic nitrite in step (ii) is selected from the group consisting of sodium nitrite and potassium nitrite.

5. The process as claimed in claim 1, wherein step (ii) is carried out at temperatures in the range from 5 to 40° C.

6. The process as claimed in claim 1, wherein the molar ratio of hydroxyl group in the alkanol or dialkanol to inorganic nitrite is in the range from 1:1.0 to 1:1.2.

7. The process as claimed in claim 1, wherein the residence time of the reactants in the reaction zone is in the range from 20 minutes to 5 hours.

8. The process as claimed in claim 1, wherein the pH of the reaction mixture at the downstream end of step (ii) is above 3.

9. The process as claimed in claim 1, wherein the alkanol or dialkanol is a linear or branched $C_2C_6$alkanol or dialkanol.

10. The process as claimed in claim 9, wherein the $C_2$-$C_6$-alkanol is selected from the group consisting of n-butanol, sec-butanol, isobutanol, tert-butanol and isoamyl alcohol.

11. The process as claimed in claim 9, wherein the $C_2$-$C_6$-dialkanol is neopentyl glycol.

12. The process as claimed in claim 1, wherein the acid equivalents per mole of hydroxyl group in the alkanol or dialkanol are on average not more than 1.00 mol.

* * * * *

UNITED STATES PATENT AND TRADEMARK OFFICE
CERTIFICATE OF CORRECTION

| | | |
|---|---|---|
| PATENT NO. | : 7,314,948 B2 | Page 1 of 1 |
| APPLICATION NO. | : 10/485209 | |
| DATED | : January 1, 2008 | |
| INVENTOR(S) | : Kudis et al. | |

It is certified that error appears in the above-identified patent and that said Letters Patent is hereby corrected as shown below:

Col. 6, indicated line 43:

"$C_2C_6$alkanol" should read --$C_2$-$C_6$-alkanol--

Signed and Sealed this

Twenty-ninth Day of April, 2008

JON W. DUDAS
*Director of the United States Patent and Trademark Office*